United States Patent
Han et al.

(10) Patent No.: US 9,445,776 B2
(45) Date of Patent: Sep. 20, 2016

(54) X-RAY IMAGING APPARATUS AND METHOD OF CONTROLLING THE SAME

(71) Applicant: SAMSUNG ELECTRONICS CO., LTD., Suwon-si (KR)

(72) Inventors: Seok Min Han, Seongnam-si (KR); Young Hun Sung, Hwaseong-si (KR); Dong Goo Kang, Suwon-si (KR); Sung Hoon Kang, Suwon-si (KR); Sung Su Kim, Yongin-si (KR); Hyun Hwa Oh, Hwaseong-si (KR); Kang Eui Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 322 days.

(21) Appl. No.: 14/104,391

(22) Filed: Dec. 12, 2013

(65) Prior Publication Data
US 2014/0185761 A1 Jul. 3, 2014

(30) Foreign Application Priority Data

Dec. 27, 2012 (KR) ................. 10-2012-0154935

(51) Int. Cl.
*A61B 6/00* (2006.01)
*H04N 5/32* (2006.01)
*A61B 6/04* (2006.01)

(52) U.S. Cl.
CPC ............... *A61B 6/50* (2013.01); *A61B 6/4452* (2013.01); *A61B 6/4476* (2013.01); *A61B 6/461* (2013.01); *A61B 6/463* (2013.01); *A61B 6/502* (2013.01); *A61B 6/5217* (2013.01); *A61B 6/5235* (2013.01); *A61B 6/5252* (2013.01); *H04N 5/32* (2013.01); *A61B 6/0414* (2013.01); *A61B 6/486* (2013.01)

(58) Field of Classification Search
None
See application file for complete search history.

(56) References Cited

U.S. PATENT DOCUMENTS

| | | | |
|---|---|---|---|
| 8,199,878 B2* | 6/2012 | Schoenmaekers | A61B 6/484 378/57 |
| 9,025,840 B2* | 5/2015 | Waechter-Stehle | G06T 7/2053 378/98.12 |
| 2008/0037702 A1* | 2/2008 | Vallee | A61B 6/481 378/29 |
| 2010/0060633 A1* | 3/2010 | Van Hoorebeke | A61B 6/484 345/419 |
| 2012/0321156 A1* | 12/2012 | Waechter-Stehle | G06T 7/2053 382/130 |
| 2014/0185761 A1* | 7/2014 | Han | A61B 6/50 378/62 |

FOREIGN PATENT DOCUMENTS

| | | |
|---|---|---|
| KR | 1020040054791 A | 6/2004 |
| KR | 1020110060899 A | 6/2011 |
| KR | 1020120010639 A | 2/2012 |
| KR | 1020120018758 A | 3/2012 |

* cited by examiner

*Primary Examiner* — Thomas R Artman
(74) *Attorney, Agent, or Firm* — Sughrue Mion, PLLC

(57) ABSTRACT

Disclosed are an X-ray imaging apparatus that captures one or more images of an inner part of the human body or the like, and a method for controlling the apparatus. In particular, an imaging system includes an X-ray generator which is configured to irradiate a target object with X-rays, a detector which is configured to detect X-rays which are emitted at a plurality of times and which have propagated through the target object, a driver which is configured to change a position of the X-ray generator or the detector, an image processor which is configured to generate a plurality of X-ray images from the detected X-rays and to compare the plurality of X-ray images in order to generate at least one difference image, and a controller which is configured to detect tissues which constitute the target object based on the at least one difference image.

10 Claims, 20 Drawing Sheets

X-RAY IMAGING APPARATUS AND METHOD OF CONTROLLING THE SAME

CROSS-REFERENCE TO RELATED APPLICATION(S)

This application claims priority from Korean Patent Application No. 10-2012-0154935, filed on Dec. 27, 2012 in the Korean Intellectual Property Office, the disclosure of which is incorporated herein by reference in its entirety.

BACKGROUND

1. Field

Exemplary embodiments relate to an X-ray imaging apparatus that captures an image of an inner part of the human body or the like in order to generate an image, and a method for controlling the apparatus.

2. Description of the Related Art

An X-ray imaging apparatus, such as, for example, an X-ray radiography apparatus, a computed tomography (CT) scanner, a full field digital mammography (FFDM) apparatus, or the like, is a medical system which irradiates a target object, such as the human body with X-rays, receives X-rays which have propagated through the target object, reads out an X-ray image from the received X-rays, and indicates the X-ray image to a doctor, a diagnostician, or the like.

An X-ray radiography system of such an X-ray imaging apparatus generates an image of a target object, such as, for example, an inner part of the human body, by using attenuation characteristics whereby X-rays pass through or are absorbed into a material based on a density of the material.

In detail, with regard to an X-ray image acquisition process of such an X-ray radiography system, when a voltage is applied such that electrons are accelerated in order to collide with a material, the electrons are decelerated by Coulombic force in a vicinity of an atomic nucleus in order to emit electromagnetic waves. Here, the generated electromagnetic waves, that is, X-rays, are emitted toward a target object, X-rays which have propagated through the target object are received and converted into an electrical signal, and then, an X-ray image is read out from the electrical signal in order to acquire an image.

Thus, with respect to a high density portion of the target object, inner materials of which are relatively dense, or a low density portion of the target object, it is difficult to accurately detect tissues which constitute an inner part of the target object by using only such an X-ray imaging apparatus.

SUMMARY

Therefore, it is an aspect of one or more exemplary embodiments to provide an X-ray imaging apparatus and a method for controlling the same, which are improved to clearly and easily a target object or tissues which constitute the target object, which are unclear and obscure in a conventional X-ray captured image.

Additional aspects of the exemplary embodiments will be set forth in part in the description which follows and, in part, will be obvious from the description, or may be learned by practice of the exemplary embodiments.

Thus, an X-ray imaging apparatus and a method for controlling the same are provided.

In accordance with an aspect of one or more exemplary embodiments, an X-ray imaging apparatus includes an X-ray generator which is configured to emit X-rays toward a target object at different positions, a driver which is configured to move the X-ray generator to change a position thereof, a detector which is configured to detect a plurality of X-rays which have propagated through the target object, an image processor which is configured to generate a plurality of X-ray images from the detected plurality of X-rays and to compare the generated plurality of X-ray images in order to generate at least one difference image, and a controller which is configured to detect at least one tissue which constitutes the target object from the generated at least one difference image.

The image processor may be further configured to extract a plurality of boundary data from the generated plurality of X-ray images and to perform a comparison operation between the extracted plurality boundary data in order to acquire the at least one difference image. The image processor may be further configured to generate an image of the at least one tissue which constitutes the target object and to combine the generated image of the at least one tissue which constitutes the target object with one image from among the generated plurality of X-ray images in order to generate a display image.

In accordance with another aspect of one or more exemplary embodiments, an X-ray imaging apparatus includes an X-ray generator which is configured to emit X-rays toward a target object a plurality of times, a detector which is configured to receive a plurality of X-rays which have propagated through the target object, a driver which is configured to move the detector in order to change a position thereof, an image processor which is configured to generate a plurality of X-ray images from the detected plurality of X-rays and to generate at least one difference image by using the generated plurality of X-ray images, and a controller which is configured to detect at least one tissue which constitutes the target object from the at least one difference image.

The image processor may be further configured to extract a plurality of boundary data from the generated plurality of X-ray images and to perform a comparison operation between the extracted plurality of boundary data in order to acquire the at least one difference image. The image processor may be further configured to generate an image of the at least one tissue which constitutes the target object and to combine the generated image of the at least one tissue which constitutes the target object with one image from among the generated plurality of X-ray images in order to generate a display image.

In accordance with another aspect of one or more exemplary embodiments, a method for controlling an X-ray imaging apparatus includes moving at least one of an X-ray generator and an X-ray detector and emitting X-rays at a plurality of relative positions therebetween in order to acquire a plurality of X-ray images, generating at least one difference image based on the acquired plurality of X-ray images, and determining a modified portion which corresponds to a difference between at least two of the acquired plurality X-ray images based on the generated at least one difference image in order to detect at least one tissue which constitutes the target object by using the determined modified portion.

The method may further include generating an image of the at least one tissue which constitutes the target object, and combining the generated image of the at least one tissue which constitutes the target object with one image from among the acquired plurality of X-ray images in order to generate a display image.

The generating the at least one difference image may include irradiating, by an X-ray generator, the target object with X-rays at a first position in order to acquire first X-ray data of the target object, and irradiating, by the X-ray generator, the target object with X-rays at a second position which is different from the first position.

The generation of the at least one difference image may include extracting a plurality of boundary data from the acquired plurality of X-ray images and performing a comparison operation between the extracted plurality of boundary data in order to generate the at least one difference image. The generation of the at least one difference image may include performing a comparison operation between corresponding pixels of a first X-ray image from among the acquired plurality of X-ray images and a second X-ray image from among the acquired plurality of X-ray images in order to generate a difference image with respect to the first and second X-ray images.

In accordance with another aspect of one or more exemplary embodiments, a method for controlling an X-ray imaging apparatus includes emitting, by an X-ray generator, X-rays toward a target object based on a change in a distance between the X-ray generator and an X-ray detector in order to acquire a plurality of X-ray images, generating at least one difference image by using the acquired plurality of X-ray images, and combining the generated at least one difference image with one image from among the acquired plurality of X-ray images in order to generate a display image.

The generation of the at least one difference image may include irradiating, by the X-ray generator, the target object with X-rays at a first position in order to acquire first X-ray data of the target object and irradiating, by the X-ray generator, the target object with X-rays at a second position which is different from the first position.

The generation of the at least one difference image may include extracting a plurality of boundary data from the acquired plurality of X-ray images and performing a comparison operation between the extracted plurality of boundary data in order to generate the at least one difference image. The generation of the at least one difference image may include performing a comparison operation between respective pixels of a first X-ray image from among the acquired plurality of X-ray images and respective pixels of a second X-ray image from among the acquired plurality of X-ray images in order to generate a difference image with respect to the first and second X-ray images.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Hereinafter, an overall structure of an X-ray imaging apparatus according to an exemplary embodiment will be described with reference to FIGS. 1 through 6.

Figure 1:
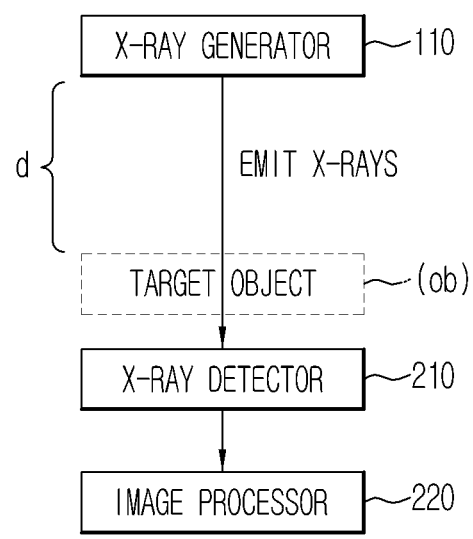
FIG. 1 is a conceptual diagram of an X-ray imaging apparatus, according to an exemplary embodiment.

FIG. 1 is a conceptual diagram of an X-ray imaging apparatus, according to an exemplary embodiment.

As shown in FIG. 1, the X-ray imaging apparatus according to the present exemplary embodiment includes an X-ray generator 110 which is configured to generate X-rays and irradiate a target object ob with the X-rays, an X-ray detector 210 (hereinafter, referred to as the detector 210) which is configured to receive X-rays which have propagated through the target object ob, to detect a plurality of X-rays, and to convert the received and/or detected X-rays into electrical signals, and an image processor 220 which is configured to read out an image from the electrical signal which is output from the detector 210 and to perform a predetermined image process on the image.

The X-ray generator 110 may be configured to irradiate the target object ob with X-rays a plurality of times, and the detector 210 may be configured to receive the X-rays which are emitted from the X-ray generator 110 a plurality of times, convert the received X-rays into a plurality of electrical signals, and store and output the electrical signals.

In particular, the X-ray generator 110 and the detector 210 are spaced apart from each other by a predetermined distance d. According to an exemplary embodiment, the X-ray generator 110 may emit X-rays at various positions in order to acquire X-ray images with respect to a plurality of positions while a relative position of the X-ray generator 110 with respect to the detector 210 is changed by moving the X-ray generator 110 or the detector 210. For example, as described later with reference to FIG. 10, while changing the predetermined distance d between the X-ray generator 110 and the detector 210, respective X-ray images which are captured at a corresponding plurality of distances d may be acquired.

In order to change the relative position between the X-ray generator 110 and the detector 210, a driver 120 (see, e.g., FIG. 2) which is configured to drive at least one of the X-ray generator 110 and the detector 210 may be coupled to one or both of the X-ray generator 110 and the detector 210.

The plurality of X-ray images which respectively correspond to the plurality of electrical signals which are stored and output by the detector 210 are generated by the image processor 220. In particular, the image processor 220 reads out the plurality of electrical signals which are stored or output by the detector 210 in order to generate the plurality of X-ray images.

According to an exemplary embodiment, the image processor 220 may perform a difference operation with respect to the plurality of X-ray images in order to generate at least one difference image which is based on the plurality of X-ray images.

In some exemplary embodiments, the image processor 220 may search for a modified portion with respect to the plurality of X-ray images by using the generated difference image. In addition, the image processor 220 may detect at least one tissue which constitutes the target object ob from the modified portion in order to additionally generate separate data which is related to the detected tissues, and in order to display the data to a user.

Alternatively, according to an exemplary embodiment, the image processor 220 may generate a new display image by combining the generated difference image and at least one image which is selected from among the plurality of X-ray images which are captured at the various distances d by using an overlap method or the like.

Figure 2:
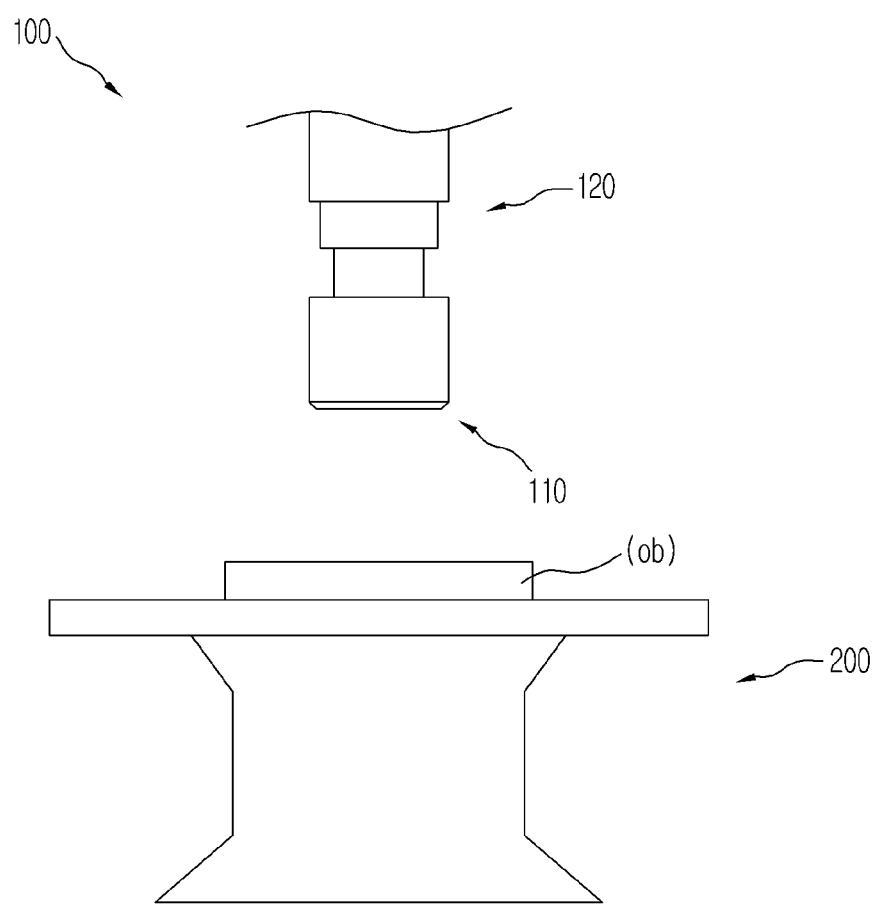
FIG. 2 is a side view of an X-ray imaging apparatus, according to an exemplary embodiment.
Figure 3:
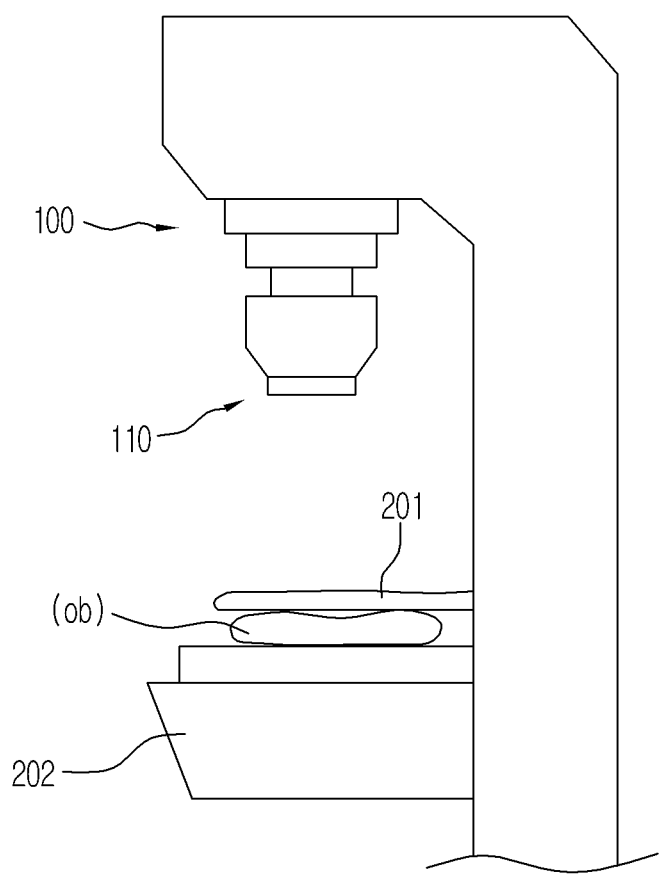
FIG. 3 is a side view of an X-ray imaging apparatus, according to another exemplary embodiment.

Hereinafter, the X-ray imaging apparatus will be described in detail based on the aforementioned concept thereof. FIGS. 2 and 3 are side views of an X-ray imaging apparatus, according to an exemplary embodiment.

As shown in FIG. 2, according to the present exemplary embodiment, the X-ray imaging apparatus may be a digital radiography (DR) apparatus. The DR apparatus includes an X-ray generation module 100, which includes the X-ray generator 110 which is configured to generate X-rays and to irradiate the target object ob with the X-rays and the driver 120 which is coupled to the X-ray generator 110 and which is configured to drive the X-ray generator 110, as described above, and an X-ray detection module 200, which includes the detector 210 which is configured to support the target object ob and to receive the X-rays which are emitted by the X-ray generator 110.

According to another exemplary embodiment, as illustrated in FIG. 3, a medical imaging apparatus, that is, the X-ray imaging apparatus, may be a mammography apparatus. Similarly, the mammography apparatus includes the X-ray generation module 100, which includes the X-ray generator 110 which is configured to generate X-rays and to irradiate the target object ob with the X-rays and the driver 120 which is coupled to the X-ray generator 110 and which is configured to drive the X-ray generator 110. In addition, the mammography apparatus may include the detector 210, which may include a platform 202 which is configured to support the target object ob, e.g. a breast, and which detector 210 is configured to receive the X-rays which are emitted from the X-ray generator 110. In addition, the mammography apparatus may further include a separate compression paddle 201 which is configured to compress the target object ob, that is, the breast.

In addition, although not shown, for example, other imaging apparatuses which use X-rays, such as, for example, a computed tomography (CT) apparatus, may be used as the X-ray imaging apparatus.

Hereinafter, the X-ray imaging apparatus will be described in more detail with reference to FIGS. 4, 5, and 6.

Figure 4:
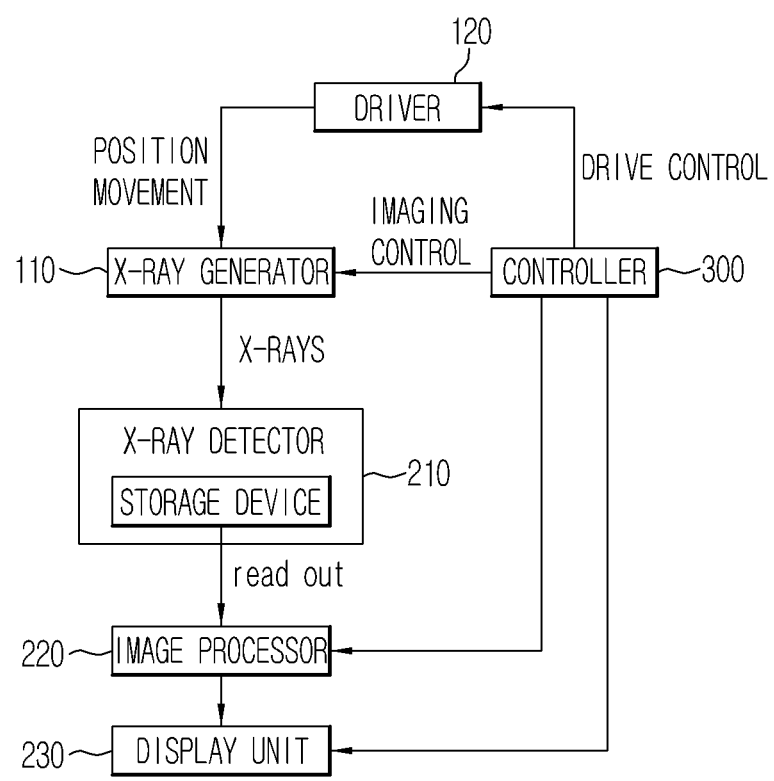
FIG. 4 is a block diagram of a structure of an X-ray imaging apparatus, according to an exemplary embodiment.

FIG. 4 is a block diagram of an X-ray imaging apparatus, according to an exemplary embodiment.

As shown in FIG. 4, according to the present exemplary embodiment, the X-ray imaging apparatus may include the X-ray generator 110 which is configured to emit X-rays, the driver 120 which is connected to the X-ray generator 110, the detector 210 which is configured to receive and detect the X-rays which are emitted by the X-ray generator 110 and to convert the detected X-rays into electrical signals, the image processor 220 which is configured to read out or generate an image from the electrical signals which are converted via the detector 210 or to perform a predetermined image process on the read out or generated image, a display unit 230 which is configured to display the image which is read out or generated by the image processor 220 to a user, for example, a doctor or a patient, and a controller 300 which is configured to control the X-ray generator 110, the driver 120, the image processor 220, and the display unit 230.

Here, all elements 110 through 230 may be implemented in one X-ray diagnosis apparatus. As necessary, the elements 110 through 230 may be distributed in a plurality of apparatuses, such as, for example, an X-ray radiography apparatus which is configured to perform X-ray imaging and detection functions, a separate computing apparatus which is connected to the X-ray radiography apparatus in a wired or wireless manner, and the like. Thus, in the exemplified case, the computing apparatus may perform some of the functions of the image processor 220, for example, a process for generation of a difference image. In addition, the elements 110 through 230 may be distributed in respective physically subdivided devices.

Figure 5:
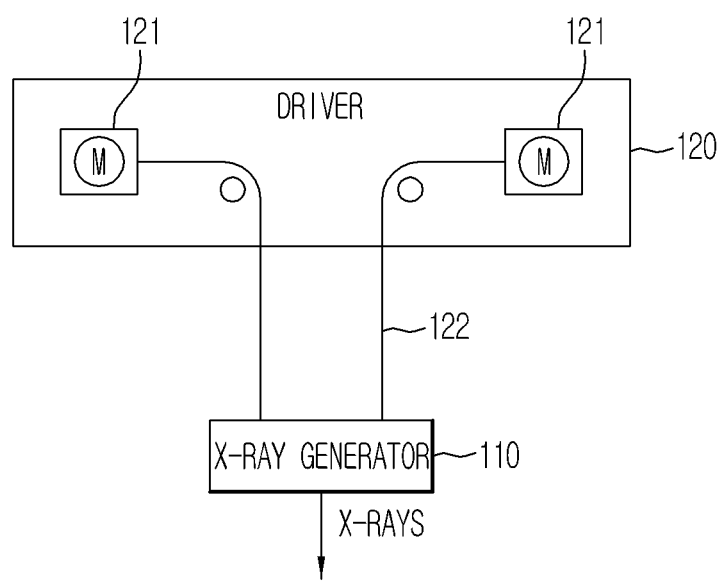
FIG. 5 is a conceptual diagram which illustrates a driver and an X-ray generator of an X-ray imaging apparatus, according to an exemplary embodiment.

FIG. 5 is a conceptual diagram which illustrates the driver 120 and the X-ray generator 110 of an X-ray imaging apparatus, according to an exemplary embodiment. As shown in FIGS. 4 and 5, according to an exemplary embodiment, the driver 120, which is configured to move the X-ray generator 110 to a predetermined position, may be coupled to the X-ray generator 110.

Referring to FIG. 4, the controller 300 controls a driving of the driver 120, and the driver 120 moves the X-ray generator 110 up and down and right and left or to a predetermined position which is selected by a user based on a control of the controller 300.

FIG. 5 shows an example of a case in which the X-ray generator 110 is moved by using a motor 121 and a cable 122, which are an example of the driver 120. In particular, the cable 122 may be moved in an upward or downward direction based on a rotation of the motor 121, and correspondingly, the X-ray generator 110 may also be moved in an upward or downward direction.

Of course, the driver 120 is not limited to the aforementioned example. For example, although not shown, the driver 120 may include a robot arm which is combined with the X-ray generator 110 and which controls the X-ray generator 110 to move to a predetermined position, and/or the driver 120 may include at least one guide rail which is installed in the X-ray generation module 110 and a motor, a pulley, or the like in order to move the X-ray generator 110 in an upward or downward direction along the guide rail, and/or may include any one or more of various types of apparatuses which are configured for changing a position.

When the X-ray generator 110 is moved based on a control of the controller 300 and the driver 120, the controller 300 provides a control command for generation of X-rays and for emission of the X-rays to the X-ray generator 110 and thereby causes the X-rays to be emitted in a predetermined direction, in particular, in a direction toward a target object. The emitted X-rays are received and detected by the detector 210 described below.

Hereinafter, the detector 210 will be described with regard to an exemplary embodiment with reference to FIGS. 4 and 6.

Figure 6:
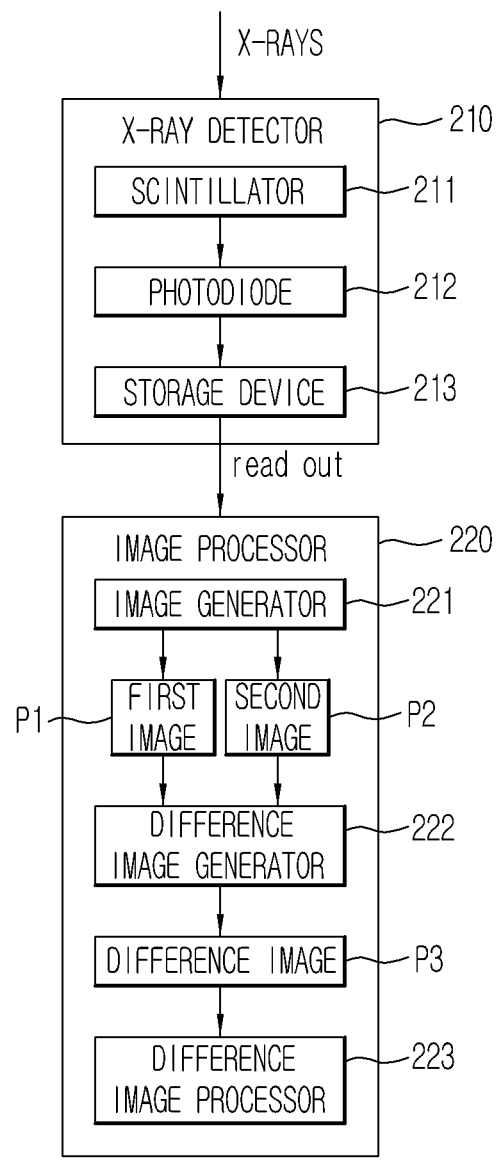
FIG. 6 is a block diagram of a detector and an image processor of an X-ray imaging apparatus.

FIG. 6 is a block diagram of the detector 210 and the image processor 220 of an X-ray imaging apparatus. According to an exemplary embodiment, the detector 210 receives X-rays that are emitted from the X-ray generator 110 and which propagate or do not propagate through a target object.

In detail, as shown in FIG. 6, the detector 210 includes a scintillator 211, a photodiode 212, and a storage device 213.

The scintillator 211 includes a material upon which radiation, such as X-rays are incident, thereby causing a scintillation phenomenon, and the scintillator receives X-rays which are emitted from the X-ray generator 110 and uses the received X-rays to generate light. Then, the photodiode 212 converts the generated light into electrical signals. The electrical signals which are converted by the photodiode 212 are stored in the storage device 213, which may include, for example, a storage capacitor or the like. Finally, the detector 210 detects X-rays.

The electrical signals stored in the storage device 213 are read out by the image processor 220.

According to an exemplary embodiment, as shown in FIG. 6, the image processor 220 may include an image generator 221, a difference image generator 222, and a difference image processor 223.

The image generator 221 reads out the electrical signals which are stored in the storage device 213 based on a control of the controller 300 or predetermined settings, and generates an X-ray image based on the read-out electrical signals. In particular, the image generator 221 may generate a plurality of images, for example, two images, that is, at least a first image P1 and a second image P2 when one target object is irradiated with X-rays a plurality of times, for example, two times.

According to an exemplary embodiment, the difference image generator 222 may generate at least one difference image based on the above-described acquired X-ray images, for example, the first image P1 and the second image P2.

The difference image refers to an additional image which is generated by comparing and calculating a difference between images with respect to a plurality of images. In detail, the difference image is generated by extracting a predetermined image value, such as, for example, an RGB value, a shading value, or the like, from each respective pixel of one image, calculating a difference between respective image values of corresponding pixels of the plurality of images from among the extracted pixels in order to obtain result values, arranging the result values at positions which correspond to the respective pixels, performing a comparison operation between the plurality of images in order to obtain results, and indicating the obtained results as the difference image. Thus, as shown in FIG. 13, the difference image may be displayed to be divided into a portion in which a difference between images is apparent to a viewer and a portion in which a difference between images is not apparent to the viewer, so as to easily display and indicate changes between images.

For example, the difference image may be displayed such that a portion in which a difference between two images is not apparent to a viewer has low brightness, that is, is displayed dark, and has higher brightness, that is, is displayed lighter, as a difference between the two images increases. In this case, a region having a large difference between two images has very high brightness, that is, is displayed very light. Thus, by virtue of the difference image, the presence or degree of a difference between a plurality of images may be displayed in one image by using brightness or the like.

The difference image generator 222 of the image processor 220 may generate a difference image P3 from a plurality of X-ray images, for example, the first image P1 and the second image P2, and store the difference image P3 in a separate storage device to as to perform a separate process upon the difference image P3.

The difference image generator 222 may extract a plurality of boundary data from a plurality of X-ray images, for example, the first image P1 and the second image P2, and compare the extracted plurality of boundary data in order to generate the difference image P3, which will be described below.

Likewise, when the difference image generator 222 generates at least one difference image P3, the at least one difference image P3 may be used by the controller 300 and/or by the difference image processor 223.

The controller 300 identifies and detects one or more tissues which constitute the human body from the at least one difference image P3.

For example, as described above, the difference image may indicate a difference between a plurality of images by using a brightness difference. In this regard, the controller 300 determines a specific portion, for example, a portion having high brightness, that is, a portion displayed light, as shown in FIG. 13, as being a difference between images, and thereby determines that a target object or at least one tissue which constitutes the target object is present in the determined portion. The determination regarding the presence of the tissues which constitute the target object will be described with reference to FIGS. 10 through 13.

According to an exemplary embodiment, the difference image processor 223 performs a predetermined image process upon the difference image which is generated by the difference image generator 222. For example, the difference image processor 223 may generate an image of tissues which constitute the target object ob, which are detected based on the at least one difference image P3, and combine the image of the tissues which constitute the target object ob with one image from among a plurality of images, for example, the first image P1 or the second image P2, in order to generate a display image.

Figure 7:
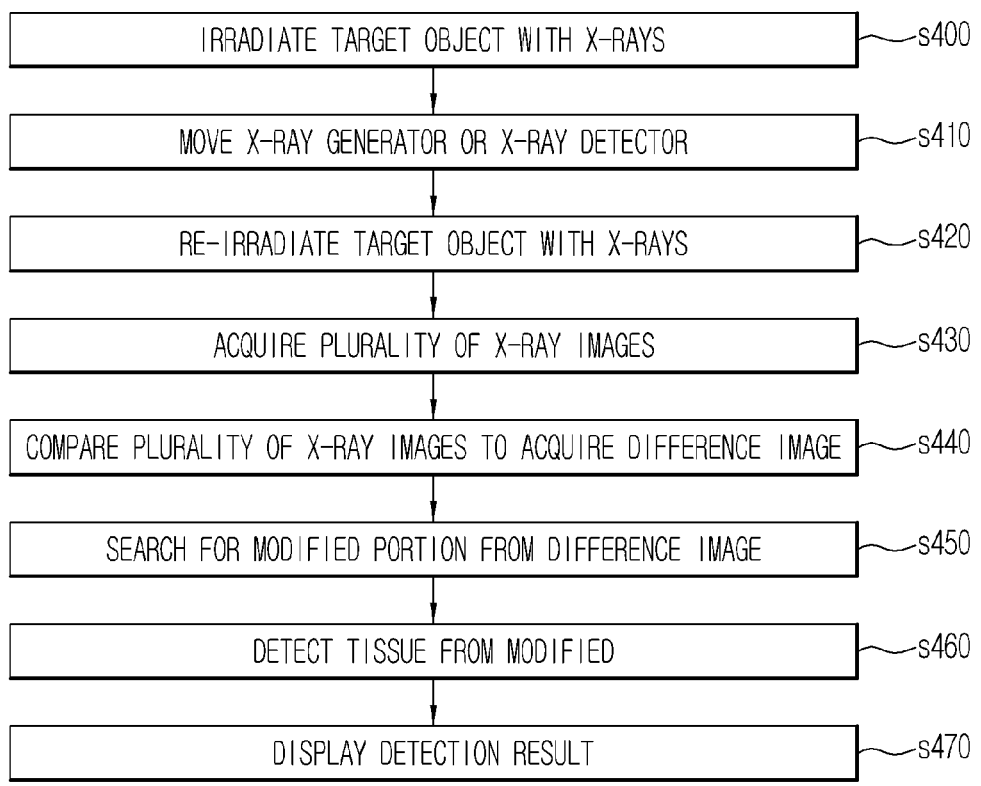
FIG. 7 is a flowchart which illustrates a method for controlling an X-ray imaging apparatus, according to an exemplary embodiment.

FIG. 7 is a flowchart which illustrates a method for controlling an X-ray imaging apparatus, according to an exemplary embodiment.

As shown in FIG. 7, according to the present exemplary embodiment, in the method for controlling the X-ray imaging apparatus, first, in operation s400, the X-ray generator 110 irradiates the target object ob with X-rays at a predetermined position. According to an exemplary embodiment, the detector 210 may detect the X-rays which are emitted toward the target object ob from the X-ray generator 110, convert the X-rays into electrical signals, and store the electrical signals, and the image processor 220 may read out the electrical signals to generate an X-ray image.

Then, in operation s410, the X-ray generator 110 or the detector 210 is controlled to be moved to a different position from the original predetermined position. For example, as shown in FIG. 8A and FIG. 8B, either or both of the X-ray generator 110 and the detector 210 may be moved.

Figure 8A:
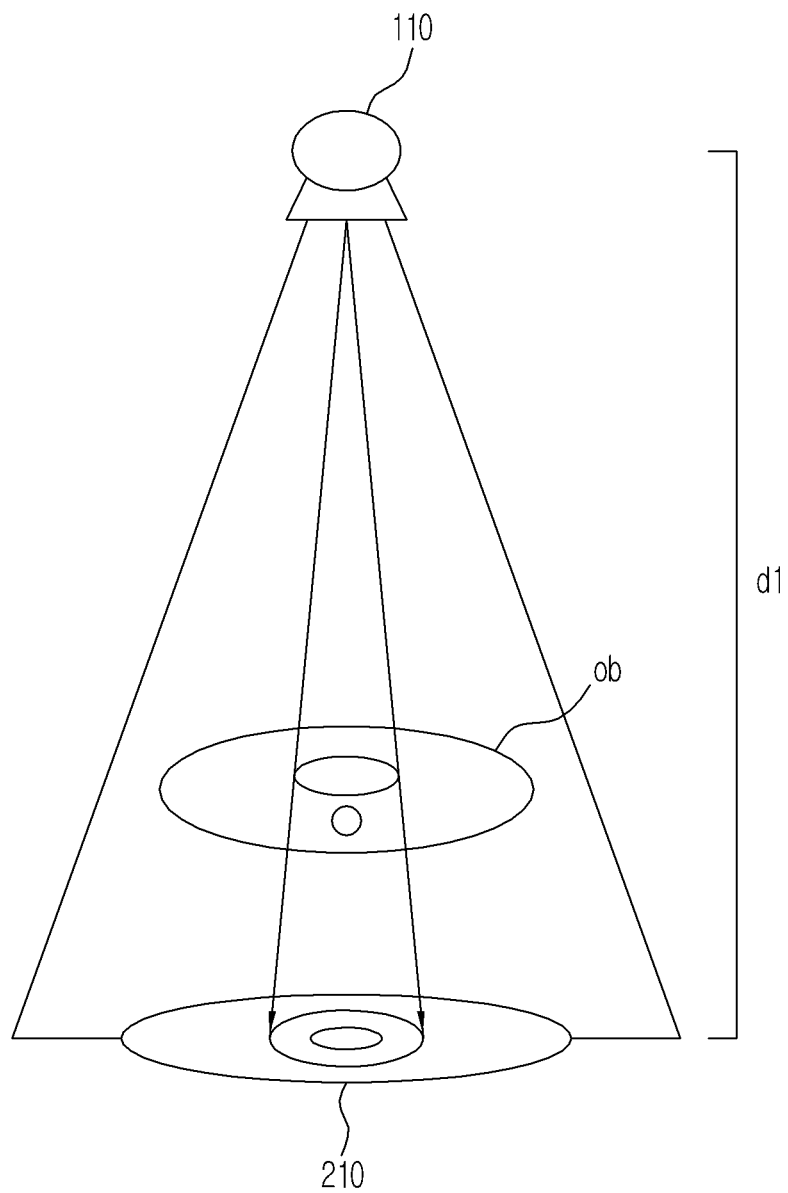
FIGS. 8A and 8B are diagrams which illustrate a distance change with respect to a method for controlling an X-ray imaging apparatus.
Figure 8B:
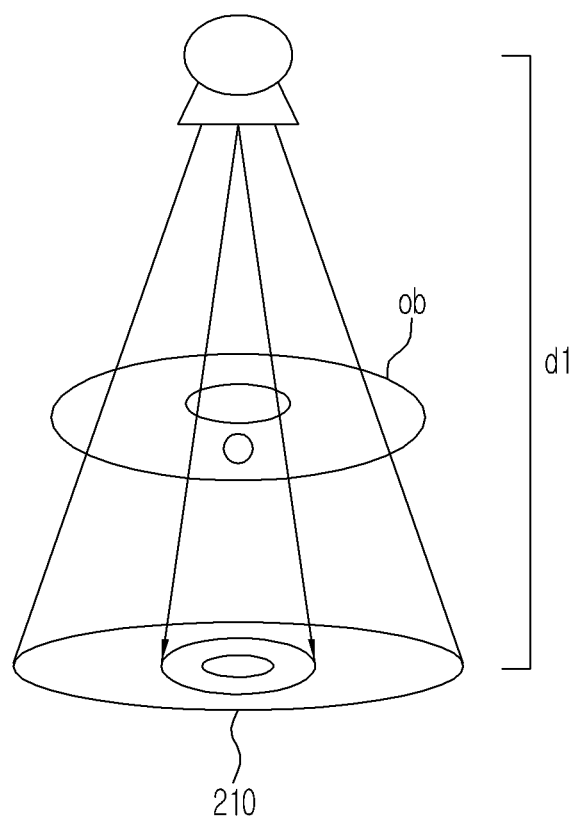

FIGS. 8A and 8B are diagrams which illustrate a distance change with respect to a method for controlling an X-ray imaging apparatus. As shown in FIG. 8, according to an exemplary embodiment, in operation s410, the X-ray generator 110 or the detector 210 may be moved in opposite directions in order to reduce a distance d therebetween (d1→d2), or in order to increase the distance therebetween (d2→d1). As described above, according to an exemplary embodiment, the driver 120 may move one or both of the X-ray generator 110 and the detector 210.

Figure 9A:
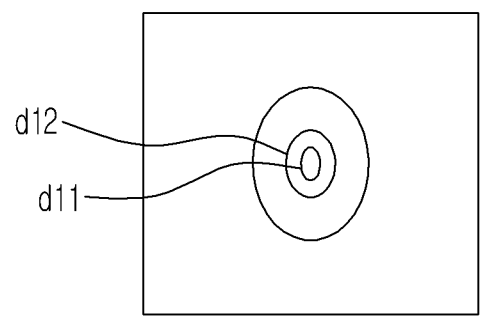
FIGS. 9A and 9B are diagrams which illustrate a difference between captured images based on a distance difference with respect to a method for controlling an X-ray imaging apparatus.
Figure 9B:
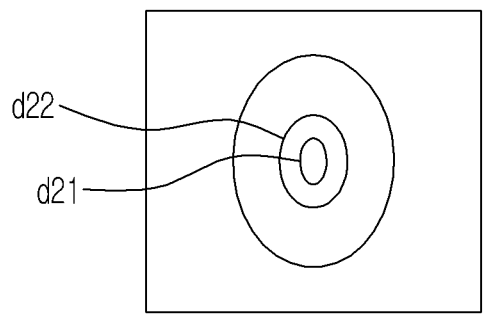

Accordingly, a relative position between the X-ray generator 110 and the detector 210, for example, the distance d between the X-ray generator 110 and the detector 210 is changed (for example, d1→d2) as described above, and then, for example, as shown in FIGS. 8A and 8B, and in operation s420, the X-ray generator 110 re-irradiates the target object ob with X-rays. Then, in operation s430, a plurality of X-ray images, such as, for example, X-ray images as shown in FIGS. 9A and 9B, are acquired. Operations s410 and s420 may be repeatedly performed a plurality of times, as necessary.

In addition, in operation s440, a difference image (see, e.g., FIG. 11) with respect to a plurality of X-ray images (such as, for example, the images illustrated in FIGS. 9A and 9B) is acquired from the acquired plurality of X-ray images.

Figure 10:
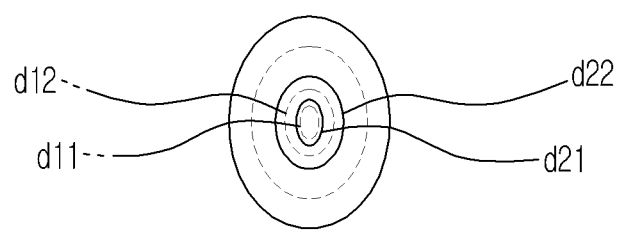
FIG. 10 is another diagram which illustrates a difference between captured images based on a distance difference with respect to a method for controlling an X-ray imaging apparatus.

FIGS. 9A and 9B are diagrams which illustrate a difference between captured images based on a distance difference with respect to a method for controlling an X-ray imaging apparatus, and FIG. 10 is another diagram which illustrates a difference between captured images which is based on a distance difference with respect to a method for controlling an X-ray imaging apparatus.

FIG. 9A shows an X-ray image which is captured at a distance d1 between the X-ray generator 110 and the detector 210, and FIG. 9B shows an X-ray image which is captured at a distance d2 between the X-ray generator 110 and the detector 210. Here, d1>d2, as illustrated, for example, in FIGS. 8A and 8B.

The X-ray image shown in FIG. 9A is captured when a distance between the X-ray generator 110 and the detector 210 is relatively long, that is, a long distance d1, and thus, a target object d12 or a tissue d11 therein may be displayed relatively small based on to the rules of perspective. Conversely, the X-ray image shown in FIG. 9B is displayed when the distance between the X-ray generator 110 and the detector 210 is relatively short, that is, a short distance d2, and thus, a target object d22 or a tissue d21 therein may be displayed relatively large as compared with a case of the long distance d1. In this aspect, images which are obtained by imaging the target object d12 and the inner tissue d11 at the short distance d1 and images which are obtained by imaging the target object d22 and the inner tissues d11 and d12 at the long distance d1 are inevitably different from one another.

Such a difference may clearly be seen with reference to FIG. 10. FIG. 10 is obtained by performing an overlap between the image of FIG. 9A and the image of FIG. 9B. As seen from FIG. 10, in the overlap image, respective outlines of the target objects d12 and d22 are different, and respective outlines of the inner tissues d11 and d21 are different, and a difference between the image shown in FIG. 9A and the image shown in FIG. 9B corresponds to a region between the respective outlines of the target objects d12 and d22 and a region between the respective outlines of the inner tissues d11 and d21.

The difference image more visually indicates such a difference so as to more clearly determine the difference. The difference image will be described in more detail with reference to FIG. 11.

Figure 11:
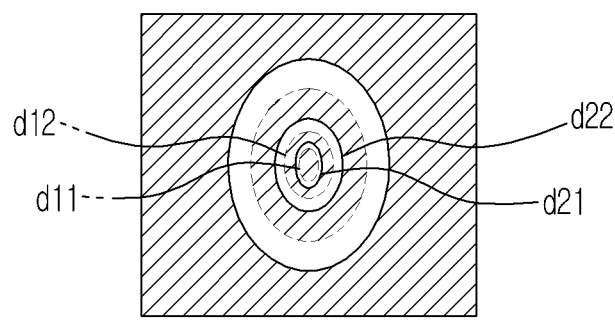
FIG. 11 is a diagram which illustrates a difference image which is obtained based on a method for controlling an X-ray imaging apparatus.

FIG. 11 is a diagram which illustrates a difference image which is obtained by executing a method for controlling an X-ray imaging apparatus.

FIG. 11 shows the difference image between the images shown in FIGS. 9A and 9B, which is generated by performing a difference operation with respect to brightness values of corresponding pixels of the images in order to obtain result values, that is, difference operation result values, arranging the difference operation result values at positions corresponding to the respective pixels to generate brightness values, and comparing the generated brightness values.

In FIG. 11, a light region indicates a region in which a difference between the two images is present and a dark region indicates a region in which a difference between the two images is not present. In particular, as described with reference to FIG. 10, the region in which the difference between the two images is present is displayed light, and the region in which the difference between the two images is not present is displayed dark. Thus, the region between the outlines of the inner tissues d11 and d21 and the region between the target objects d12 and d22 are displayed light (white), and the remaining regions are displayed dark (black), because the remaining regions are not changed.

In some exemplary embodiments, a method for generating a difference image may include, for example, a method for generating a difference image by separating partial images from an image of a target object in order to generate a difference image by using the separated images, as well as a method for generating the difference image by performing a comparison operation, for example, a difference operation with respect to a difference between images with regard to a plurality of images.

Figure 12A:
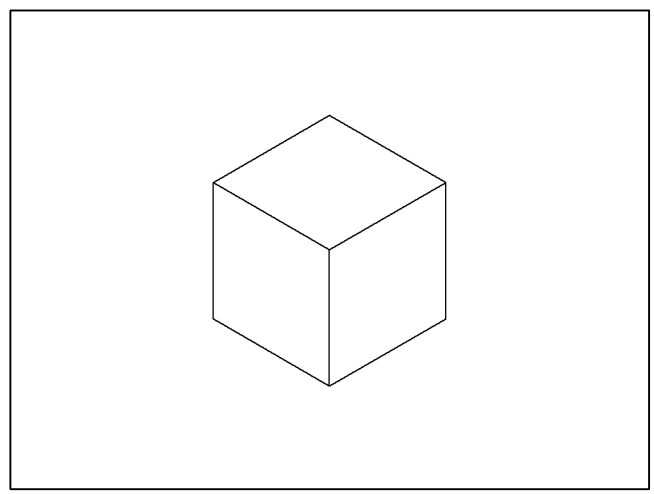
FIGS. 12A, 12B, 13A, 13B, and 14 are diagrams which illustrate an acquisition of a difference image based on a method for controlling an X-ray imaging apparatus, according to another exemplary embodiment.
Figure 12B:
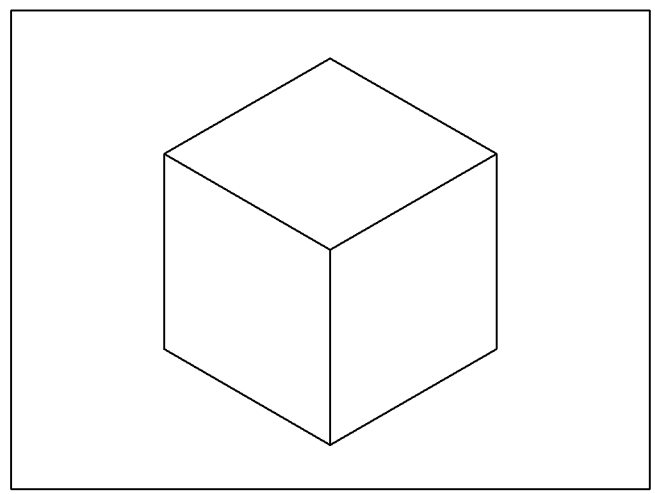

FIGS. 12A, 12B, 13A, 13B, and 14 are diagrams which illustrate an acquisition of a difference image in a method for controlling an X-ray imaging apparatus, according to another exemplary embodiment. FIGS. 12A and 12B show X-ray images which are captured by imaging a target object at respective distances d1 and d2. An image captured at a long distance is shown in FIG. 12A, and an image captured at a short distance is shown in FIG. 12B.

A method for acquiring a difference image according to another exemplary embodiment will be described below.

Figure 13A:
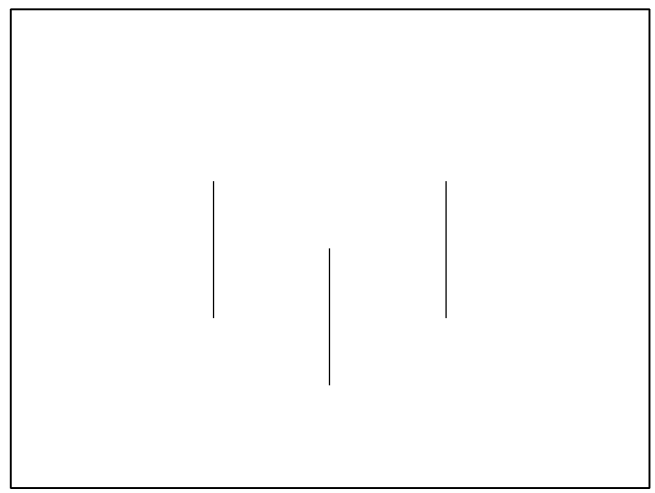
Figure 13B:
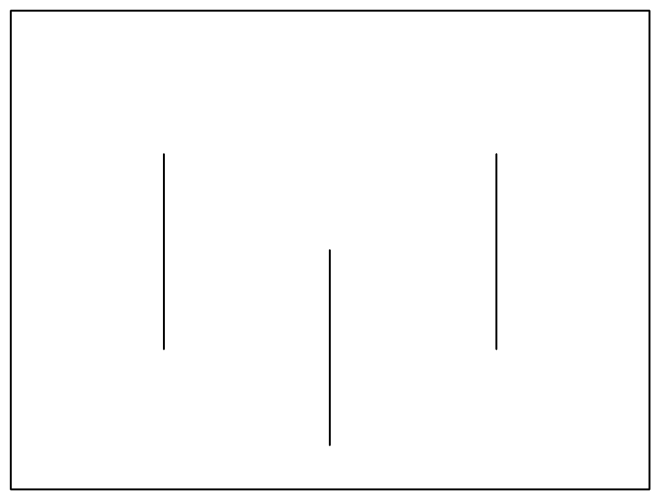

First, with regard to the images shown in FIGS. 12A and 12B, only specific direction outlines, for example, vertical outlines of the target object, are extracted from among outlines of the target object. Thus, data shown in FIGS. 13A and 13B, such as, for example, image information, may be acquired, which is referred to as feature extraction. With regard to the feature extraction, extracted features may be arbitrarily selected. For example, with regard to the feature extraction, as shown in FIGS. 13A and 13B, only the vertical outlines of the target object may be extracted. Similarly, horizontal outlines of the target object may be extracted, or predominant features may be selected from an image.

When the feature extraction is performed, partial data instead of entire data of an image may be used to perform an image process, for example, the aforementioned difference operation, to thusly reduce a data processing amount, thereby increasing a data processing speed, for example, a speed of generating the difference image.

Figure 14:
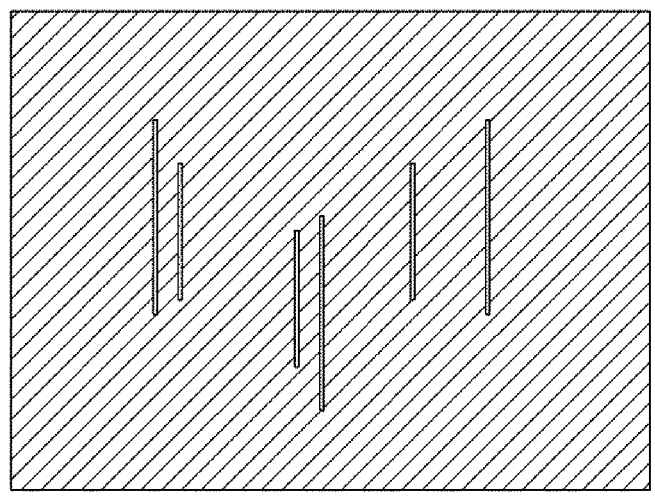

As shown in FIGS. 12A, 12B, 13A, and 13B, additional images of the respective X-ray images may be acquired from the respective X-ray images via the feature extraction, and then, the aforementioned comparison operation is performed on the additional images to thusly generate a difference image, as shown in FIG. 14.

As seen from FIG. 14, the difference image which is obtained after the feature extraction of the image is displayed such that regions having differences among the extracted features are distinguished from regions which do not have differences among the extracted features. That is, for example, as shown in FIG. 14, the regions having differences among the extracted features may be displayed light (i.e., as indicated by white lines of FIG. 14) and the regions which do not have differences among the extracted features may be displayed dark.

Likewise, in some exemplary embodiments, the comparison operation, for example, a difference operation, may be performed between extracted features of two images in order to generate a difference image.

Although not shown, in some exemplary embodiments, the above-described operation with regard to the various exemplary embodiments may be performed in order to generate a difference image, and then, the difference image may be displayed directly on the display unit 230, such as, for example, a monitor. In this case, a doctor or a diagnostician may easily and quickly detect an unclear and obscure target object or tissues which constitute the target object from an X-ray captured image with reference to the difference image.

As described above, according to an exemplary embodiment, after the difference image is generated, an operation of removing predetermined noise may be further performed on the difference image. An X-ray imaging apparatus may perform an imaging operation a plurality of times, for example, at least two times, and thus, unnecessary noise may be generated during X-ray emission and detection processes, or during an image processing process. Such noise may impede a correct determination of variation of tissues inside the target object, and thus, it may be useful to remove the noise in advance.

According to an exemplary embodiment, as a method of removing noise, when a result value of a difference operation with respect to each pixel is within a predetermined range, the result value may be reset to zero or to another predetermined value. According to another exemplary embodiment, when a result value with respect to a predetermined pixel is excessively great or small compared with those of adjacent pixels, the result value with respect to the predetermined pixel may instead be corrected to an average value of the result values of the adjacent pixels.

In operation s450, a modified portion is searched for from the aforementioned generated difference image. For example, as shown in FIG. 11 or 14, a portion which is displayed light to a predetermined level or more is detected from the image, and for example, information which relates to the shape or position of the portion is separately stored in order to facilitate a search for the modified portion. In this case, according to an exemplary embodiment, the portion which is displayed light to a predetermined level or more may be detected by determining whether or not a result value of a difference operation with respect to pixels of the portion is within a predetermined range. When the result value of the difference operation is within the predetermined range, the portion is regarded as the modified portion, and this process may be repeatedly performed on all pixels in order to completely extract modified portions from the difference image.

When the modified portion is detected as described above, in operation s460, a target object or tissues which constitute the target object are detected from the modified portion. In particular, when the modified portion is detected, it is determined that the target object or the tissues which constitute the target object are present in a region in which the modified portion is detected, and thus, the target object or the tissues which constitute the target object are detected.

A process for determining that the target object or the tissues which constitute the target object are present in the region in which the modified portion is detected will now be described in more detail. As described above, when the X-ray generator 110 or the detector 210 is moved to cause a difference in a distance therebetween, a target object or tissues which constitute the target object which have been imaged at each distance may inevitably have a different size or may have different positions due to change in an imaging position, as shown in FIGS. 12A and 12B. Thus, the difference in size and imaging position may be displayed by the difference image, and for example, may be displayed light, as described with reference to FIG. 11 or FIG. 14.

Conversely, when a target object or tissues which constitute the target object are not present in a plurality of captured images, the plurality of captured images may be completely or almost the same, and thus, the difference image may be displayed dark, as described with reference to FIG. 11 or FIG. 14.

Thus, it may be determined that the target object or the tissues which constitute the target object are present in or near the modified portion, that is, the region displayed dark as shown in FIG. 11 or FIG. 14, and thus, the target object or the tissues which constitute the target object may be detected from the modified portion of the difference image.

According to an exemplary embodiment, when the target object or the tissues which constitute the target object are detected, in operation s470, a detection result may be finally indicated to a user in order to inform the user of the presence or position of the target object or the tissues which constitute the target object. In this case, the presence, presence possibility, positions, or predicted shapes of the target object or tissues may be indicated to the user as numerical data. As necessary, information which relates to the target object or the tissues, which is acquired from the difference image, may be processed in order to form a separate image or the like. In addition, as described above, the difference image may be displayed directly on the display unit 230.

Figure 15:
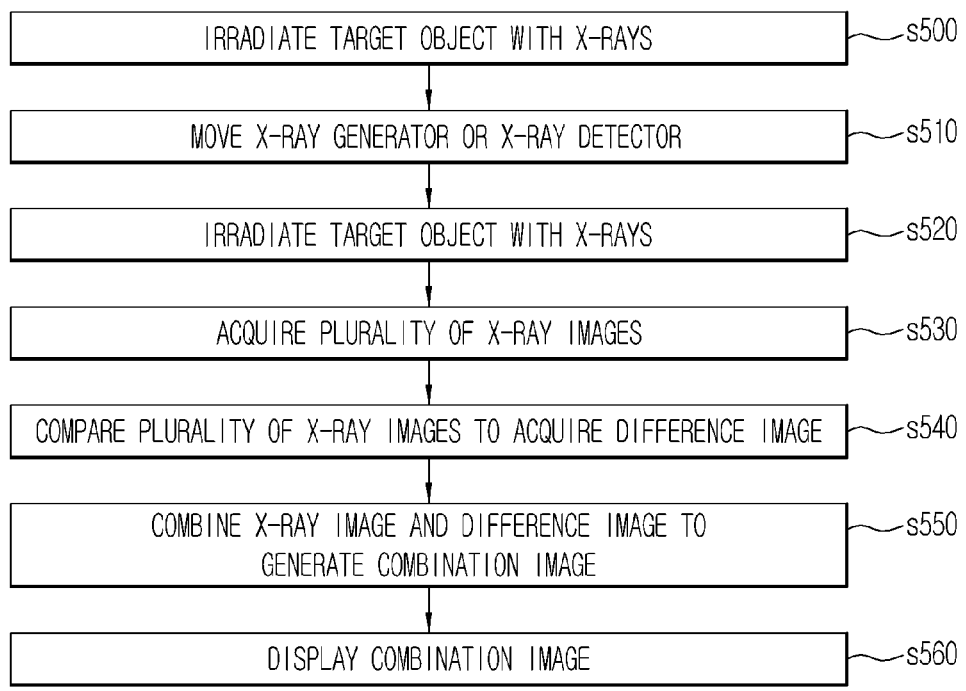
FIG. 15 is a flowchart which illustrates a method for controlling an X-ray imaging apparatus, according to another exemplary embodiment.

FIG. 15 is a flowchart which illustrates a method for controlling an X-ray imaging apparatus, according to another exemplary embodiment.

According to another exemplary embodiment, the method for controlling the X-ray imaging apparatus may include irradiating, by an X-ray generator, a target object with X-rays in operation s500, moving the X-ray generator or an X-ray detector in order to change a relative position, such as, for example, a distance, therebetween in operation s510, re-irradiating the target object with X-rays by the X-ray generator in operation s520, acquiring a plurality of X-ray images via the above-described operation or repeating the above-described operation in operation s530, calculating and generating an difference image between a plurality of X-ray images acquired as described above in operation s540, combining any one of the plurality of X-ray images and the difference image in order to generate a combination image in operation s550, and displaying the generated combination image in operation s560, as shown in FIG. 15.

Operations s500 through s550 have been described above with regard to operations s400 through s450 of FIG. 7, and thus, a further detailed description thereof will be omitted.

Figure 16:
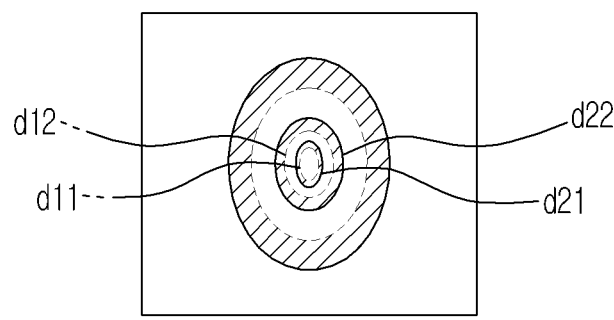
FIG. 16 is a diagram of a combination image which is generated by executing a method for controlling an X-ray imaging apparatus.

According to an exemplary embodiment, the difference image is generated via operation s500 through s540, and then, in operation s550, the difference image and a separate X-ray image, for example, any one of a plurality of X-ray images used to generate the difference image may be combined to generate a combination image, such as, for example, the image shown in FIG. 16. In some exemplary embodiments, as necessary, noise may be removed from the difference image.

FIG. 16 is a diagram of a combination image which is generated by executing a method for controlling an X-ray imaging apparatus.

For example, a difference image may be acquired as shown in FIG. 11 or FIG. 14. Only light regions may be extracted or only dark regions may be removed from the acquired difference image, and then, an X-ray image that is further combined with the light regions may be generated by performing an overlap between the difference image and a separate X-ray image, for example, any one of a plurality of X-ray images which is used to generate the difference image.

In this case, the extracted difference image may be combined with a separate X-ray image by performing an overlap between the difference image and the X-ray image by increasing the transparency of the extracted difference image.

According to an exemplary embodiment, an image processing process may be performed on a region in which a difference between images is present, for example, an image processing process may be performed on a light region of the difference image in order to cause the light region to become dark, and then, the difference image and the X-ray image may be combined.

In addition, according to an exemplary embodiment, an image processing process may be performed by increasing the width of an outline of a light region of the difference image, or by applying a separate color, for example, red to the light region, and then, the difference image is combined with a separate X-ray image such that the region in which a difference between images is present, that is, a region in which a target object or tissues which constitute the target object are present, may be more clearly displayed to a user.

For example, as shown in FIG. 16, a separate color is applied to the region in which a difference between images is present, that is, a light region of the difference image, in order to obtain an imaging effect, and then, the difference image is overlapped with any one of a plurality of X-ray images to more clearly display the region in which a difference between images is present. Thus, a doctor or a patient may easily identify or check tissues inside the human body, which may otherwise be unclear and/or difficult to identify.

According to the above-described exemplary embodiment, a separate image and the difference image may be combined in order to generate the combination image, and then, in operation s560, the combination image is displayed to a user, for example, a doctor or a diagnostician. Thus, tissues or a lesion inside a target object of X-ray imaging may be more easily or clearly detected, and moreover, the accuracy and efficiency of a diagnosis which is performed by using a medical image may be improved.

As is apparent from the above description, an X-ray imaging apparatus and a method for controlling the apparatus according to exemplary embodiments may prevent inaccuracy and unclearness of an image of a target object and/or tissues constituting the target object, unlike in a conventional X-ray imaging apparatus.

Although a few exemplary embodiments have been shown and described, it will be appreciated by those skilled in the art that changes may be made in these exemplary embodiments without departing from the principles and spirit of the present inventive concept, the scope of which is defined in the claims and their equivalents.

What is claimed is:

1. A method for controlling an X-ray imaging apparatus, the method comprising:
   detecting, by the apparatus, X-rays which have propagated through a target object at at least two different positions in order to acquire a plurality of X-ray images;
   comparing the acquired plurality of X-ray images in order to generate at least one difference image based on the acquired plurality of X-ray images; and
   determining a modified portion which corresponds to a difference between at least two of the plurality of X-ray images based on the generated at least one difference image; and
   detecting at least one tissue which constitutes the target object by using the determined modified portion,
   wherein the comparing the acquired plurality of X-ray images in order to generate the at least one difference image comprises irradiating, by an X-ray generator, the target object with X-rays at a first position in order to acquire first X-ray data of the target object, and irradiating, by the X-ray generator, the target object with X-rays at a second position which is different from the first position.

2. The method according to claim 1, further comprising generating an image of the at least one tissue which constitutes the target object, and combining the generated image of the at least one tissue which constitutes the target object with one image from among the acquired plurality of X-ray images in order to generate a display image.

3. The method according to claim 1, wherein the comparing the acquired plurality of X-ray images in order to generate the at least one difference image comprises extracting a plurality of boundary data from the acquired plurality of X-ray images and performing a comparison operation between the extracted plurality of boundary data in order to generate the at least one difference image.

4. The method according to claim 1, wherein the comparing the acquired plurality of X-ray images in order to generate the at least one difference image comprises performing a comparison operation respective pixels of a first X-ray image from among the acquired plurality of X-ray images with respective pixels of a second X-ray image from among the acquired plurality of X-ray images in order to generate a difference image with respect to the first and second X-ray images.

5. A method for controlling an X-ray imaging apparatus, the method comprising:
   detecting, by the apparatus, X-rays which have propagated through a target object at at least two different positions in order to acquire a plurality of X-ray images;
   comparing the acquired plurality of X-ray images in order to generate at least one difference image based on the acquired plurality of X-ray images; and
   combining one image from among the acquired plurality of X-ray images with the generated at least one difference image in order to generate a display image,
   wherein the generation of the at least one difference image comprises irradiating, by an X-ray generator, the target object with X-rays at a first position in order to acquire first X-ray data of the target object, and irradiating, by the X-ray generator, the target object with X-rays at a second position which is different from the first position.

6. The method according to claim 5, wherein the generation of the at least one difference image comprises extracting a plurality of boundary data from the acquired plurality of X-ray images and performing a comparison operation between the extracted plurality of boundary data in order to generate the at least one difference image.

7. The method according to claim 5, wherein the generation of the at least one difference image comprises performing a comparison operation respective pixels of a first X-ray image from among the acquired plurality of X-ray images with respective pixels from a second X-ray image from among the acquired plurality of X-ray images in order to generate a difference image with respect to the first and second X-ray images.

8. An X-ray imaging apparatus comprising:
an X-ray generator which is configured to emit X-rays toward a target object at different positions;
a detector which is configured to detect a plurality of X-rays which have propagated through the target object;
a driver which is configured to move at least one of the X-ray generator and the detector in order to change a respective position thereof;
an image processor which is configured to generate a plurality of X-ray images from the detected plurality of X-rays and to compare the generated plurality of X-ray images in order to generate at least one difference image; and
a controller which is configured to detect at least one tissue which constitutes the target object from the generated at least one difference image,
wherein the X-ray generator is further configured to irradiate the target object with X-rays at a first position in order to acquire first X-ray data of the target object, and to irradiate the target object with X-rays at a second position which is different from the first position in order to acquire second X-ray data of the target object, and the image processor is further configured to use the acquired first X-ray data and the acquired second X-ray data for generating the at least one difference image.

9. The X-ray imaging apparatus according to claim 8, wherein the image processor is further configured to extract a plurality of boundary data from the generated plurality of X-ray images and to perform a comparison operation between the extracted plurality of boundary data in order to generate the at least one difference image.

10. The X-ray imaging apparatus according to claim 8, wherein the image processor is further configured to generate an image of the at least one tissue which constitutes the target object and to combine the generated image of the at least one tissue which constitutes the target object with one image from among the generated plurality of X-ray images in order to generate a display image.

\* \* \* \* \*